(12) United States Patent
Kubena

(10) Patent No.: US 6,933,164 B2
(45) Date of Patent: Aug. 23, 2005

(54) METHOD OF FABRICATION OF A MICRO-CHANNEL BASED INTEGRATED SENSOR FOR CHEMICAL AND BIOLOGICAL MATERIALS

(75) Inventor: Randall L Kubena, Oak Park, CA (US)

(73) Assignee: HRL Laboratories, LLC, Malibu, CA (US)

( * ) Notice: Subject to any disclaimer, the term of this patent is extended or adjusted under 35 U.S.C. 154(b) by 348 days.

(21) Appl. No.: 10/231,962

(22) Filed: Aug. 30, 2002

(65) Prior Publication Data

US 2003/0045019 A1 Mar. 6, 2003

Related U.S. Application Data

(60) Provisional application No. 60/316,663, filed on Aug. 30, 2001.

(51) Int. Cl.$^7$ ............................................. H01L 21/00
(52) U.S. Cl. .............................. 438/49; 438/50; 438/52
(58) Field of Search ..................................... 438/48–54

(56) References Cited

U.S. PATENT DOCUMENTS

| | | | |
|---|---|---|---|
| 5,372,930 A | | 12/1994 | Colton et al. ................... 435/6 |
| 5,550,090 A | * | 8/1996 | Ristic et al. ................... 438/52 |
| 5,807,758 A | | 9/1998 | Lee et al. ................... 436/526 |

FOREIGN PATENT DOCUMENTS

| | | |
|---|---|---|
| EP | 0 072 744 | 2/1983 |
| WO | 94/23872 | 12/1994 |
| WO | 00/66266 | 11/2000 |

OTHER PUBLICATIONS

Fritz, J., et al., "Translating Biomolecular Recognition into Nanomechanics," *Science*, vol. 288, pp 316–318 (Apr. 14, 2000).

Ilic, B., et al., "Mechanical Resonant Immunospecific Biological Detector," *Appl. Phys. Lett.*, vol. 77, No. 3, pp 450–452 (Jul. 17, 2000.).

Maute, M., et al., "Detection of Volatile Compounds (VOCs) with Polymer Coated Cantilevers: Changes in Resonances of Thermal Noise," *Transducers*, pp 636–639 (Jun. 1999).

\* cited by examiner

*Primary Examiner*—H. Jey Tsai
(74) *Attorney, Agent, or Firm*—Ladas & Parry LLP

(57) ABSTRACT

A method for fabricating a sensor for chemical and/or biological materials, comprising steps of providing a wafer comprising a plurality of cantilever assemblies, each of the assemblies comprising a cantilever member and a micro-channel plate bonded to the cantilever member, the micro-channel plate further comprising a micro-channel, functionalizing each of the cantilevers by directing a flow of a plurality of functionalizing materials through the micro-channels, and dicing the wafer into a plurality of the sensors. Each of the cantilever assemblies comprises substrate comprising control and sense electrodes deposited on its top side and scribe marks etched on its back side; a cantilever member comprising a cantilever, a seed layer and a contact pad formed on top side of the cantilever member; and the micro-channel plate comprises a micro-channel housing defining the micro-channel etched through the housing, wherein the back side of the cantilever member is bonded to the substrate and the micro-channel plate is bonded to said top side of the cantilever member. Control electronics are incorporated into the substrate for a completely integrated design.

23 Claims, 10 Drawing Sheets

METHOD OF FABRICATION OF A MICRO-CHANNEL BASED INTEGRATED SENSOR FOR CHEMICAL AND BIOLOGICAL MATERIALS

This application claims priority under 35 U.S.C. § 119(e) to co-pending U.S. Pat. application Ser. No. 60/316,663 (filed on 30 Aug. 2001) entitled "A METHOD OF FABRICATION OF A MICRO-CHANNEL BASED INTEGRATED SENSOR FOR CHEMICAL AND BIOLOGICAL MATERIALS," the contents of which are hereby expressly incorporated herein in their entirety by this reference.

I. BACKGROUND OF THE INVENTION

1. Field of the Invention

This invention relates to the field of sensors for detecting chemical and biological materials. More particularly, it pertains to the novel technique of fabricating integrated micromachined cantilever chemical and/or biological sensors.

2. Description of the Related Art

The need for detection of chemical and/or biological agents in a variety of applications is acute. The rapid detection of very small quantities of harmful molecules, DNA, viruses, etc. using cheap throw-away sensors is particularly important.

A number of methods have been developed which allow such detection. Microelectromechanical (MEMS) technology possesses a major role in this field since MEMS sensors can be batch-processed for low cost and are capable of handling and detecting very small quantities of unknown substances. Small amounts of materials, often in the range of pico or femto liters, can be handled and measured.

In the field of MEMS sensors, cantilevers micromachined from silicon or silicon nitride with sub-millimeter lengths, widths, and thicknesses less than 10 micrometers have been used in sensors for detection of chemical and/or biological agents.

For instance, the U.S. Pat. No. 5,372,930 to Colton discloses a microfabricated cantilever which was originally developed for atomic force microscopy but was later utilized in biological and chemical sensing. The proximal probe serving as a biological and chemical sensor measures the forces arising from molecular interaction between a chemically modified probe (attached to the microfabricated cantilever) and a chemically modified surface.

Two other chemical sensors based on microfabricated cantilevers were discussed in the U.S. Pat. No. 5,807,758 to Lee, et. al.

Lee, et. al. compares these sensors with surface acoustic wave (SAW) detectors which are known to use substrates with coatings that selectively bind to target molecules of interest. When the target species binds to the coating, the additional mass of the coating will change the resonant frequency of a substrate surface acoustic wave.

One sensor discussed by Lee, et. al. utilizes the thermally induced stress produced by reactions catalyzed on the metallic coating of the cantilever. Two limitations of this sensor are that it operates most effectively in a vacuum (requiring substantial instrumentation and making it unsuitable for most biological interactions that are desired) and it is limited in specificity by the reactivity of the metal coating.

Another sensor uses the change in the resonance frequency of the cantilever due to the mass of the chemical species, in a manner analogous to the change observed in sensors using the SAW frequency. Mercury was non-specifically detected in the demonstration of the sensor, although it is noted that chemically active surfaces may be used for the specific identification of analytes.

Noting the deficiencies of the sensors mentioned above, Lee et. al. proposes a new cantilever-based sensor. The target molecule to be determined using the sensor described by Lee et. al. may be in liquid phase (in solution) or, for some embodiments of the invention, in vapor phase. A sensor according to the Lee et. al. invention, monitors whether a target species has selectively bound to groups on the cantilever surface by monitoring the displacement of the cantilever, and hence the force acting on the cantilever.

Lee's sensor has major drawbacks and disadvantages that also characterize other sensors discussed below.

Previously, in all prior art describing cantilever beams of silicon or silicon nitride used for chemical or/and biological sensors, the cantilever beams have been fabricated on a wafer, diced, and then individually coated with the functionalization material.

Thus, if different materials were needed on different cantilevers for selectivity or temperature compensation, the cantilevers needed to be spaced far enough apart so that they could be manually dipped in separate reservoirs. This prevents the integration of closely packed cantilevers in a sensor and therefore increases the size and the manufacturing costs.

In addition according to the prior art, the individual sensor dies must be functionalized serially which also increases the time and cost of manufacturing. Finally, in many previous MEMS-based chemical or/and biological sensors, the detection of the cantilever motion was determined by optical laser-based techniques. See, for example, M. Maute, et. al., Detection of Volatile Compounds with Polymer Coated Cantilevers: Changes in Resonances of Thermal Noise, *Transducers*, 1999, pp. 636–639; B. Ilic, et. al., Mechanical Resonant Immunospecific Biological Detector, *Phys. Lett.*, vol. 77, No. 3, pp. 450–452, July 2000; J. Fritz, et. al., Translating Biomolecular Recognition into Nanomechanics, Science, vol. 288, pp. 316–318, April 2000. In none of the prior art documents, were integrated control or sense electrodes incorporated for compact and low-cost sensors. Thus, these techniques yielded expensive, cumbersome and sluggish sensors.

In view of the foregoing, there is a need for a simple, inexpensive and accurate cantilever-based sensor for detection of chemical and biological materials. There is no known prior art which teaches a sensor satisfying these requirements yet a need to have such a sensor is acute.

By using the processing method of the present invention, on-chip electrostatic actuation and capacitive detection can be used for detecting resonance frequency or stress changes. These on-chip techniques provide for a sensor which is smaller, cheaper, more robust, and having improved performance not found in any other sensor device for the detection of chemical and/or biological materials.

II. SUMMARY OF THE INVENTION

The present invention describes a new method for simultaneously functionalizing or "activating" MEMS-based chemical or biological sensors with a variety of molecules for enhancing the selectivity of the sensor. This functionalization can occur on-chip using vapor phase deposition and novel microchannel-based distribution from the edge of the wafer.

Each sensor array on chip can be functionalized in parallel with different molecules before wafer dicing. This reduces the labor required to functionalize each sensor array independently. Wafer bonding and dry plasma etching are utilized for fabrication and provide a lithographic process in which a gold seed layer is coated on the individual cantilevers before functionalization.

Finally, a novel backside etching procedure is described that releases all the sensors on a wafer while preventing damage to the cantilevers or their coatings.

The purpose of this invention is threefold. First, it provides a simple and easy method for functionalizing (or coating) multiple sets of closely spaced cantilevers on an entire wafer simultaneously with different molecules. By doing that, it currently solves one of the most difficult tasks in the fabrication of chemical and/or biological MEMS sensors, which is the application of different functionalizing materials on adjacent cantilevers.

This functionalization process is performed on each die after the wafer has been fabricated and at least partially diced. Therefore, a large number of cantilever arrays can be activated simultaneously. By utilizing vapor phase deposition and micro-channel technology, this process can be automated so that a single gas manifold that is attached to the edge of the wafer can functionalize all the cantilevers on a large wafer. The number of lines in the manifold can be matched to the number of different molecules that need to be applied to different cantilevers.

Second, the method allows the integration of electrostatic and capacitive structures on the cantilever wafer for simple actuation and signal detection. By using a unique set of etching and bonding techniques, the cantilevers can be closely spaced to actuation and detection electrodes (within a few micrometers), thus eliminating higher cost, and providing improved detection techniques. These same fabrication techniques also allow a critical gold coating to be lithographically defined on the topside of the cantilevers for later binding to the functionalization layer.

Finally, it provides a method of dicing the wafer after organic coatings are applied to the cantilevers. This method allows the organic films previously applied to remain intact, while eliminating most of the stress to the devices during mechanical cleaving.

According to one aspect of the invention, a method is proposed for fabricating a sensor for chemical and/or biological materials, the method comprising the steps of providing a wafer comprising a plurality of cantilever assemblies, each of the assemblies comprising a cantilever member and a micro-channel plate bonded to the cantilever member, the micro-channel plate further comprising a micro-channel, and functionalizing each of the cantilevers by directing a flow of a plurality of functionalizing materials through the micro-channels.

According to another aspect of the invention the method for fabricating a sensor for chemical and/or biological materials, using a plurality of cantilever assemblies, each assembly comprising a substrate having a top side and a bottom side, the substrate further comprising control and sense electrodes deposited on the top side of the substrate and scribe marks etched on the back side of the substrate and having a cantilever member comprising a top side and a back side, the cantilever member further comprising a cantilever, a seed layer and a contact pad formed on the top side of the cantilever member, and including a micro-channel plate having a top side and a bottom side, the plate comprising a micro-channel housing defining the micro-channel etched through the housing, wherein the back side of the cantilever member is bonded to the substrate and the microchannel plate is bonded to the top side of the cantilever member.

III. BRIEF DESCRIPTION OF THE DRAWINGS

The features and advantages of the present invention will become better understood with regard to the following description, appended claims, and accompanying drawings.

IV. DETAILED DESCRIPTION OF THE INVENTION

The sensor which is the subject matter of the present invention preferably comprises three silicon wafers that are mechanically bonded together to produce the final structure. The fabrication process of the sensor is as follows.

Figure 1:
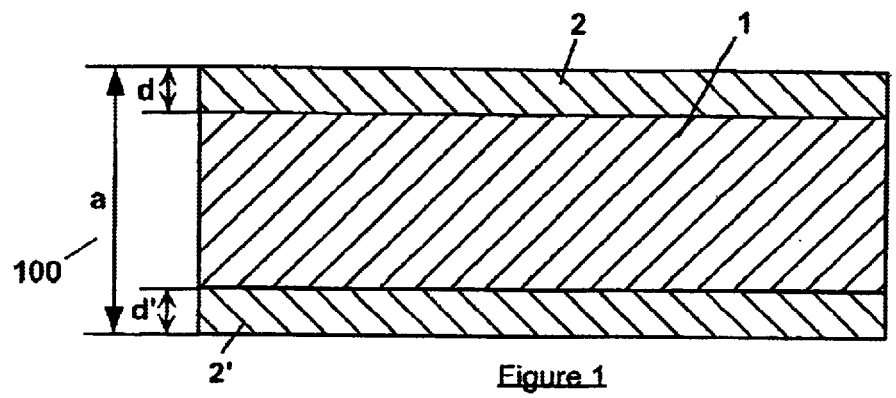
FIG. 1 is a schematic diagram showing the starting wafer (substrate) from which the method of fabrication of this invention starts.

As shown in FIG. 1, the starting wafer or substrate comprises a relatively thick wafer 100. The wafer 100 comprises a layer 1 of a semiconducting material. The semiconducting material is preferably an n-type silicon, and alternatively at least one of a Group III–Group V element. The top side of wafer 100 comprises an insulating material 2, preferably silicon oxide, or silicon nitride, $Si_3N_4$, or a combination thereof. The bottom side of wafer 100 comprises a masking material 2', preferably, $Si_3N_4$.

Total thickness, a, of the wafer 100 is within a range of between about 650 micrometers and about 850 micrometers, preferably about 750 micrometers. Each of the layers of the insulating material 2 and of the masking material 2' has a thickness, d or d', respectively (as shown in FIG. 1), within a range of between 1 micrometer and about 4 micrometers, preferably about 2 micrometers thick for each.

Figure 2:
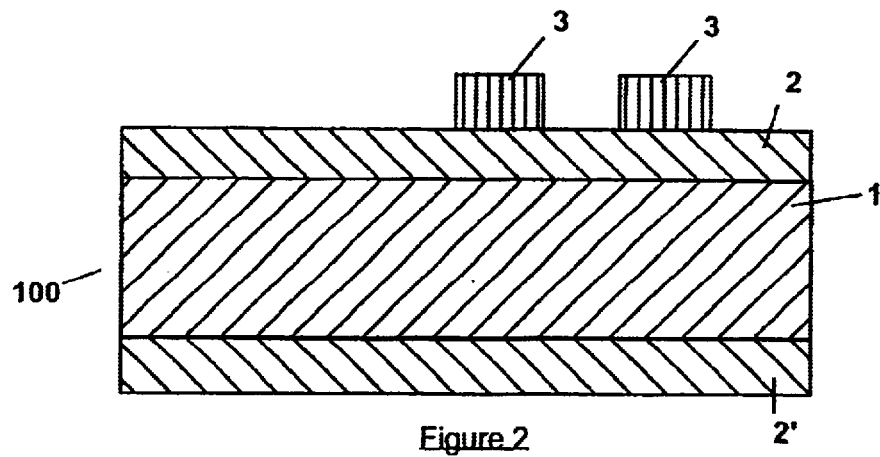
FIG. 2 is a schematic diagram illustrating the step of lithography and depositing the control and sense electrodes.

Using a method of conventional optical lithography known to those skilled in the art, control and sense electrodes 3 are deposited on the top side of the starting wafer 100 (FIG. 2).

Figure 2A:
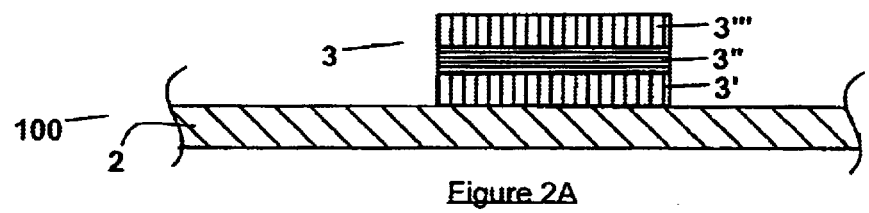
FIG. 2A is a schematic diagram showing the structure of control and sense electrodes in more detail.

As shown in FIG. 2A, these control and sense electrodes 3 comprise an adhesive layer 3' in direct contact with the insulating layer 2, the active layer 3''' on top of the electrode 3, and a diffusion barrier layer 3'' sandwiched between the adhesive layer 3' and the active layer 3'''. The adhesive layer 3' is preferably fabricated of titanium and alternatively of chromium and has a thickness within a range of between about 100 Angstroms and about 300 Angstroms, preferably about 200 Angstroms. The diffusion barrier layer 3'', is preferably fabricated of platinum and alternatively of palladium and has a thickness within a range of between about 300 Angstroms and about 700 Angstroms, preferably about 500 Angstroms. The active layer 3''' is preferably fabricated of gold and has a thickness within a range of between about 1,000 Angstroms and about 4,000 Angstroms, preferably about 2,000 Angstroms.

Figure 3:
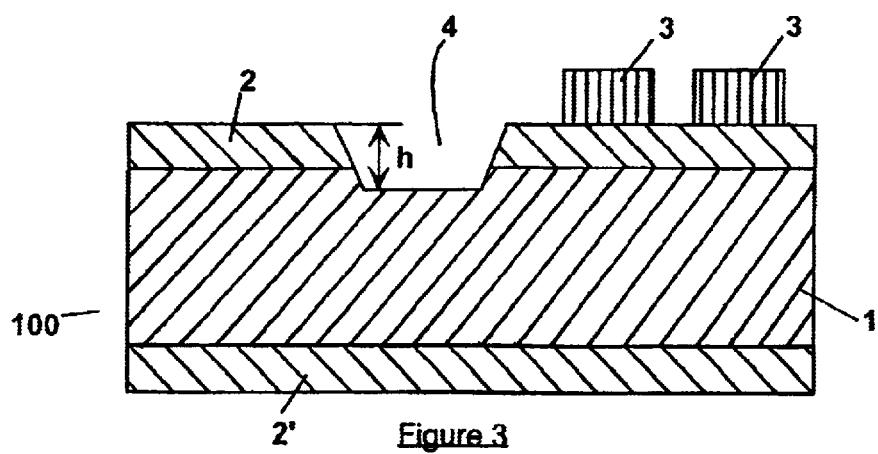
FIG. 3 is a schematic diagram illustrating the step of lithography and etching in bond regions on the front side of the starting wafer.

After the step of depositing the sense and control electrodes 3, trenches 4 are etched into the oxide layer 2 on the front side of the wafer 100 and into the layer 1, as shown in FIG. 3. The depth of the trench 4, h, is within a range of between about 150 micrometers and about 350 micrometers, preferably about 250 micrometers, and is achieved preferably by using a method of deep trench etching, the method being known to those skilled in the art.

The width of the trench 4, as well as the distance between the trench 4 and the edge of the wafer, can vary according to a design. Such width and distance will be chosen according to the criteria known to those skilled in the art.

Figure 4:
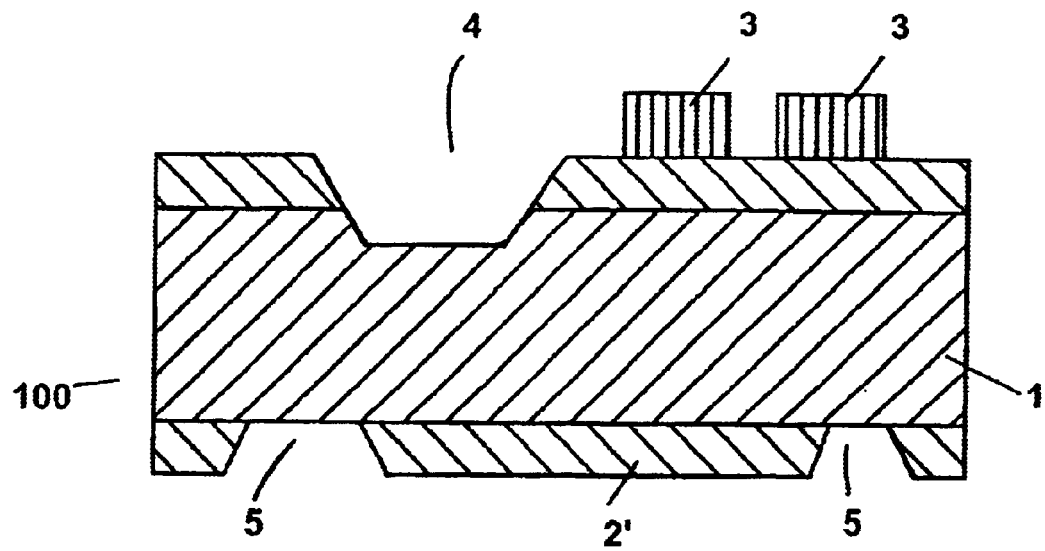
FIG. 4 is a schematic diagram illustrating the step of lithography and etching on the back side of the starting wafer.

Finally, the masking material 2' is selectively etched on the backside of the wafer 100 for defining scribe marks 5, when the masking layer 2' is completely removed. The etching stops once the layer 1 has been reached, as shown also in FIG. 4. Wet or dry etching can be used for defining the scribe marks 5, a preferred method of etching being the dry etching, such as reactive-ion etching (RIE). The width of scribe marks 5 is preferably within a range of between 10 micrometers and 100 micrometers.

Figure 5:
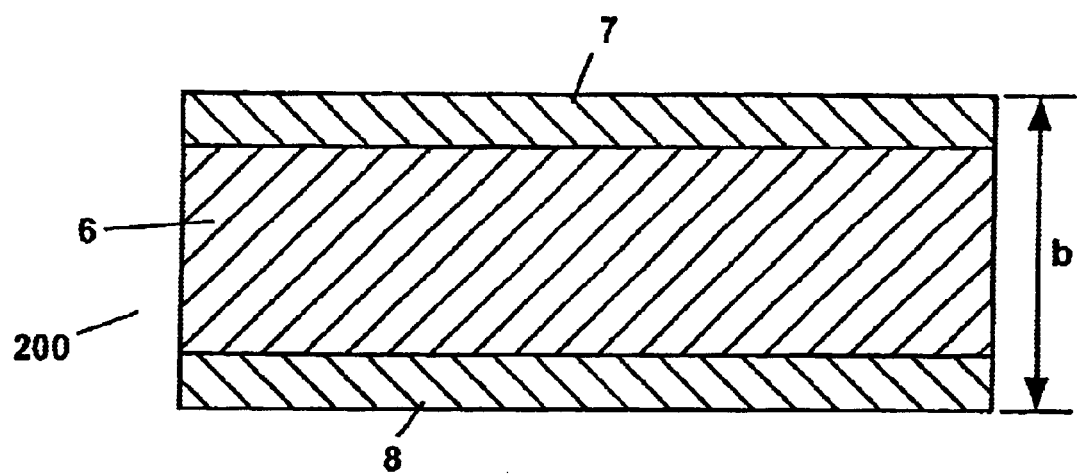
FIG. 5 is a schematic diagram showing the starting wafer from which the fabricating of the cantilever begins (the cantilever wafer).

A second, or cantilever, wafer 200 preferably comprises an n-type silicon substrate 6, as shown in FIG. 5. The total thickness, b, of the wafer 200 is within a range of between about 225 micrometers and about 375 micrometers, preferably about 275 micrometers.

The front side of the silicon layer 6 is an epitaxially grown layer of silicon 7 doped, preferably, with boron. The thickness of this layer 7 can be tailored, depending on the design of the sensor, the application and sensing mechanism, selected by those skilled in the art. Generally, the thickness of the layer 7 is within a range of between about 1 micrometer and about 5 micrometers, preferably, about 2 micrometers.

The back side of the wafer 200 comprises thermal oxide $SiO_2$, 8 (as shown in FIG. 5).

Figure 6:
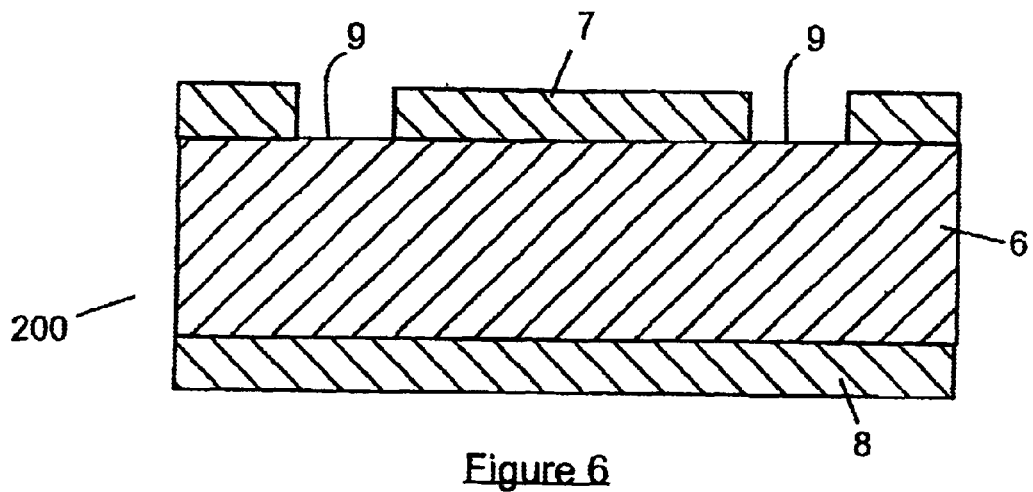
FIG. 6 is a schematic diagram illustrating the step of lithography and etching on the front side of the cantilever wafer.

The cantilever wafer 200 is processed as shown in FIGS. 6–9. First, a lithography step, as known to those skilled in the art, is performed on the front side of the cantilever wafer 200 to form the open areas 9 defining the cantilever (FIG. 6). This step is performed preferably using reactive-ion etching (RIE) or deep trench etching. These etching methods are known to those skilled in the art.

Figure 7:
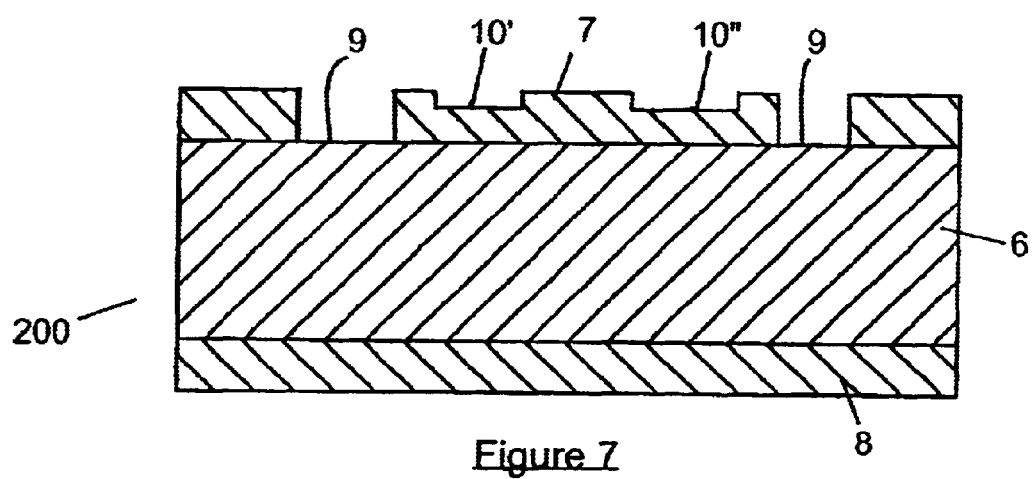
FIG. 7 is a schematic diagram illustrating the further step of processing of the cantilever wafer, comprising lithography and etching recesses on the top surface of the cantilever wafer.

The second step comprises fabricating selective recesses 10' and 10'' (FIG. 7). The recesses 10' and 10'' are etched into the boron-doped epitaxially grown layer 7 to make room for depositing a material for ohmic contact pads 11', and also for seed layer 11'', respectively, as shown on FIG. 8 and subsequently discussed.

This step of etching the recesses 10' and 10'' is performed preferably using reactive-ion etching (RIE) or deep trench etching, same as the methods used for etching the open areas 9, discussed above.

Figure 8:
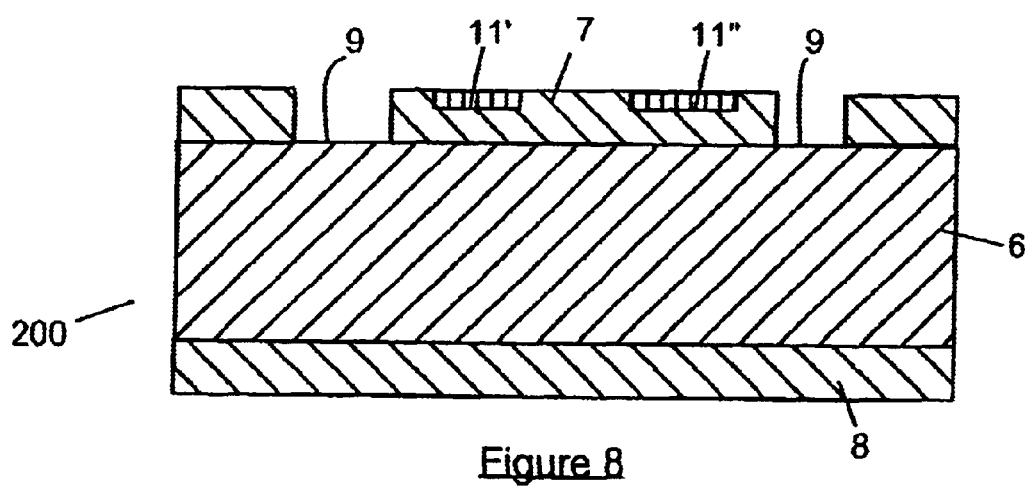
FIG. 8 is a schematic diagram showing the cantilever layer with deposited seed layer and an electrical contact pad.
Figure 8A:
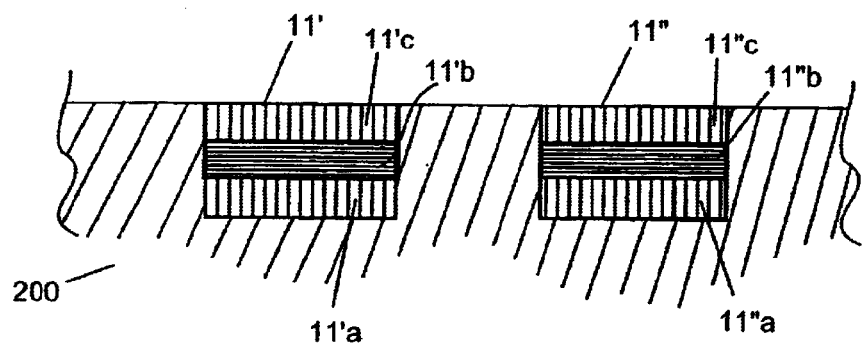
FIG. 8A is a schematic diagram showing the structure of seed layer and contact pad in more detail.

Next, a material is deposited in recesses 10' and 10'' by performing lithography and lift-off in order to define the cantilever ohmic contact pad 11' and the seed layer 11''. The process of lithography and lift-off is a widely used technique known to those skilled in the art. As shown on FIG. 8A, the ohmic contact pad 11' and the seed layer 11'' each comprise three layers: a bottom layer 11'a and 11''a respectively in direct contact with the epitaxially grown layer 7, a top layer 11'c and 11''c respectively, and a middle layer 11'b and 11''b respectively. Middle layer 11'b and 11''b are sandwiched between the bottom layer 11'a and 11''a and the top layer 11'c and 11''c, as shown in FIG. 8A.

The bottom layer 11'a and 11''a is preferably fabricated of titanium, and alternatively of chromium, and has a thickness within a range of between about 100 Angstroms and about 300 Angstroms, preferably about 200 Angstroms. The middle layers 11'b and 11''b are preferably fabricated of platinum, and alternatively of palladium, and has a thickness within a range of between about 300 Angstroms and about 700 Angstroms, preferably about 500 Angstroms. The top layer 11'c and 11''c are preferably fabricated of gold and has a thickness within a range of between about 1,000 Angstroms and about 4,000 Angstroms, preferably about 2,000 Angstroms.

The total thickness of the ohmic pad 11' and of the seed layer 11'', comprising the sum of thicknesses of the sublayers, 11'a, 11'b, and 11'c (or 11''a, 11''b and 11''c) is within a range of between about 1,400 Angstroms and about 5,000 Angstroms, preferably, between about 3,000 Angstroms.

The depth of recesses 10' and 10'' is made such as to make the top surface of the ohmic pad 11' and of the seed layer 11'' preferably be in the same plane as the top surface of the epitaxially grown layer 7. However, if the top surface of the ohmic pad 11', or of the seed layer 11'' is slightly below the surface of the layer 7, it is also acceptable.

In other words, after titanium-platinum-gold is deposited in recesses 10' and 10'', a flat top surface of the cantilever wafer 200 is where the top surface of the Ti/Pt/Au deposit is substantially aligned with the remainder of the boron-doped, epitaxially grown layer 7. This flatness is preferred (but not required) to ensure the bonding of the cantilever to the micro-channel plate wafer 300, as subsequently discussed. The flatness is ensured by computing the amount of time needed to deposit the amount of Ti/Pt/Au which will fill the recesses 10' and 10" at a chosen rate of depositing, and then to conduct the process of depositing for such calculated time.

Figure 9:
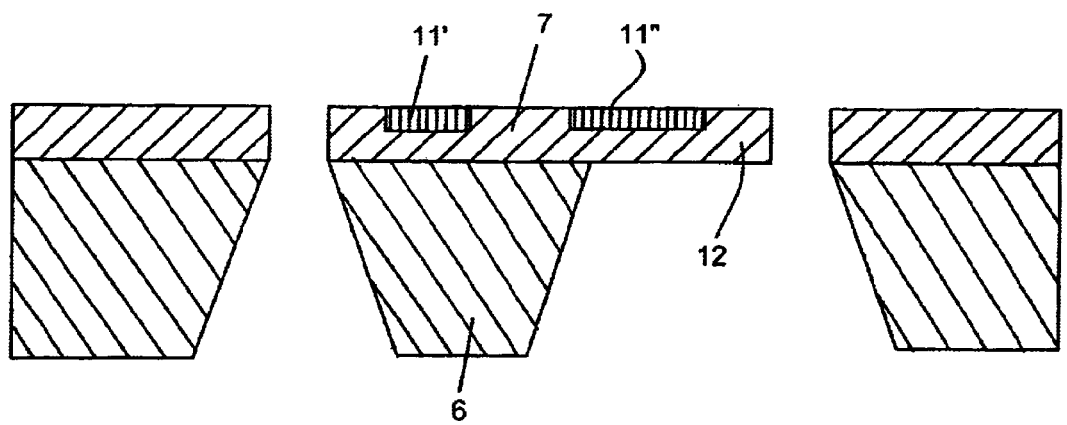
FIG. 9 is a schematic diagram illustrating the further step of processing of the cantilever wafer, comprising the backside lithography and etching to release the cantilevers.

The final processing step of the cantilever wafer 200 comprises backside lithography followed by the selective etching of the oxide layer 8, preferably by using the deep trench RIE method for defining backside wells (FIG. 9). Alternatively, the wet etching can be used.

A portion of the silicon layer 6 is then etched from the backside using ethylene diamine pyrocatechol (EDP) to release the cantilevers 12. The remaining oxide 8 is removed preferably by using a method of a plasma etching.

Alternatively, in a silicon-on-insulator (SOI) wafer, deep trench RIE could be used for etching the backside of the wafer to release the cantilevers. In this process, the backside oxide mask and the intermediate oxide layer in the SOI wafer under the cantilever could be removed at the same time.

Figure 10:
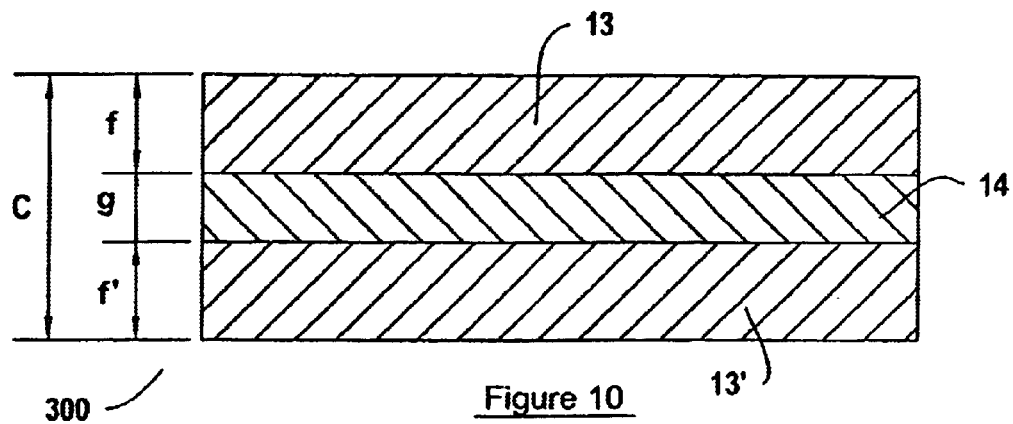
FIG. 10 is a schematic diagram showing the starting wafer for the microchannel plate from which the fabricating of the microchannels begins.

The third wafer 300 is used to fabricate the micro-channel plate. The wafer 300 has a thickness, c, within a range of between about 100 micrometers and about 400 micrometers, preferably, about 250 micrometers, and comprises an SOI structure of, preferably, a silicon oxide layer, 14, sandwiched between two layers of, preferably, silicon, 13 and 13' (FIG. 10). The top layer of silicon, 13, has a thickness, f, within a range of between about 25 micrometers and about 100 micrometers, preferably, about 50 micrometers, and the bottom layer of silicon, 13', has a thickness, f', within a range of between about 73 micrometers and about 298 micrometers, preferably, about 198 micrometers. The silicon oxide layer 14 preferably has a thickness, g, of about 2 micrometers.

Figure 11:
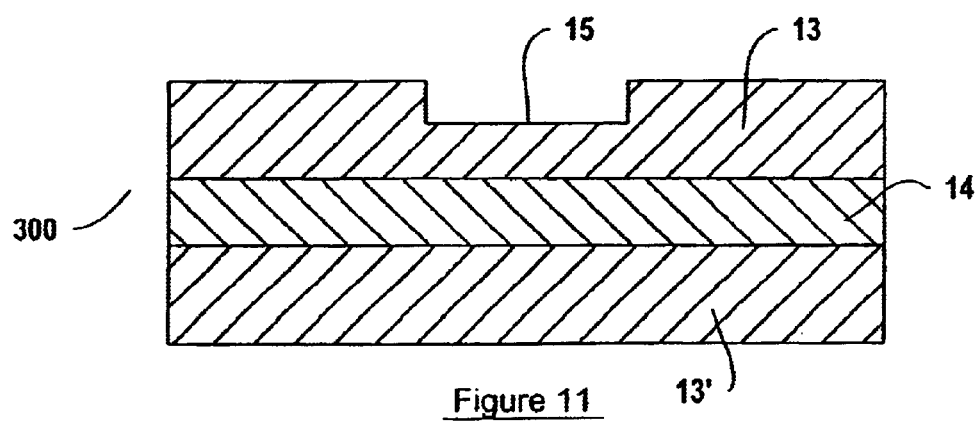
FIG. 11 is a schematic diagram illustrating the step of lithography and etching of the microchannels in the microchannel plate.

Using lithography and etching, preferably RIE, and alternatively wet etching, micro-channels 15 are first formed in the top silicon layer 13 to a preferable depth of about 10 micrometers, with a depth of up to about 70 micrometers being acceptable (FIG. 11).

Figure 12:
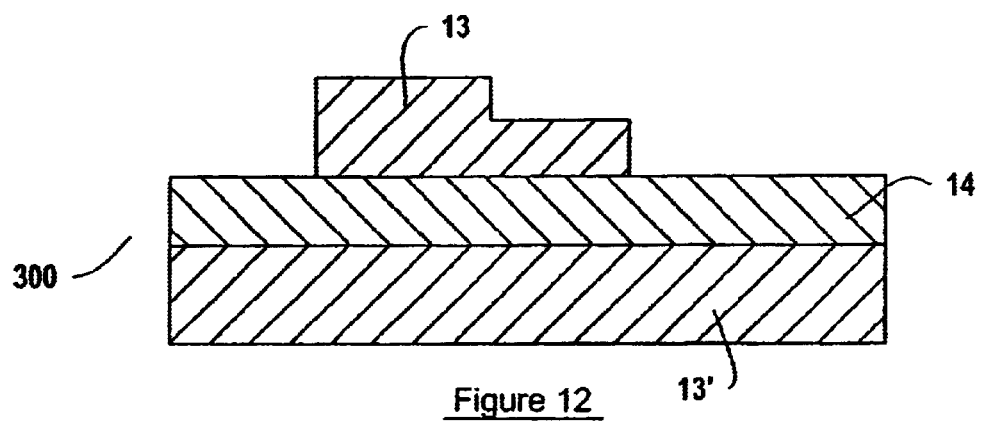
FIG. 12 is a schematic diagram illustrating the step of lithography and etching of the microchannels, housing in the top layer of the microchannel plate.

Next, deep trench etching is used to define a micro-channel housing 13' that will be bonded to the cantilever epitaxially grown layer 7 (FIG. 12). The length of the micro-channel is preferably under about 100 micrometers. These micro-channels will be used to separately dose each cantilever with a specific molecule.

Figure 13:
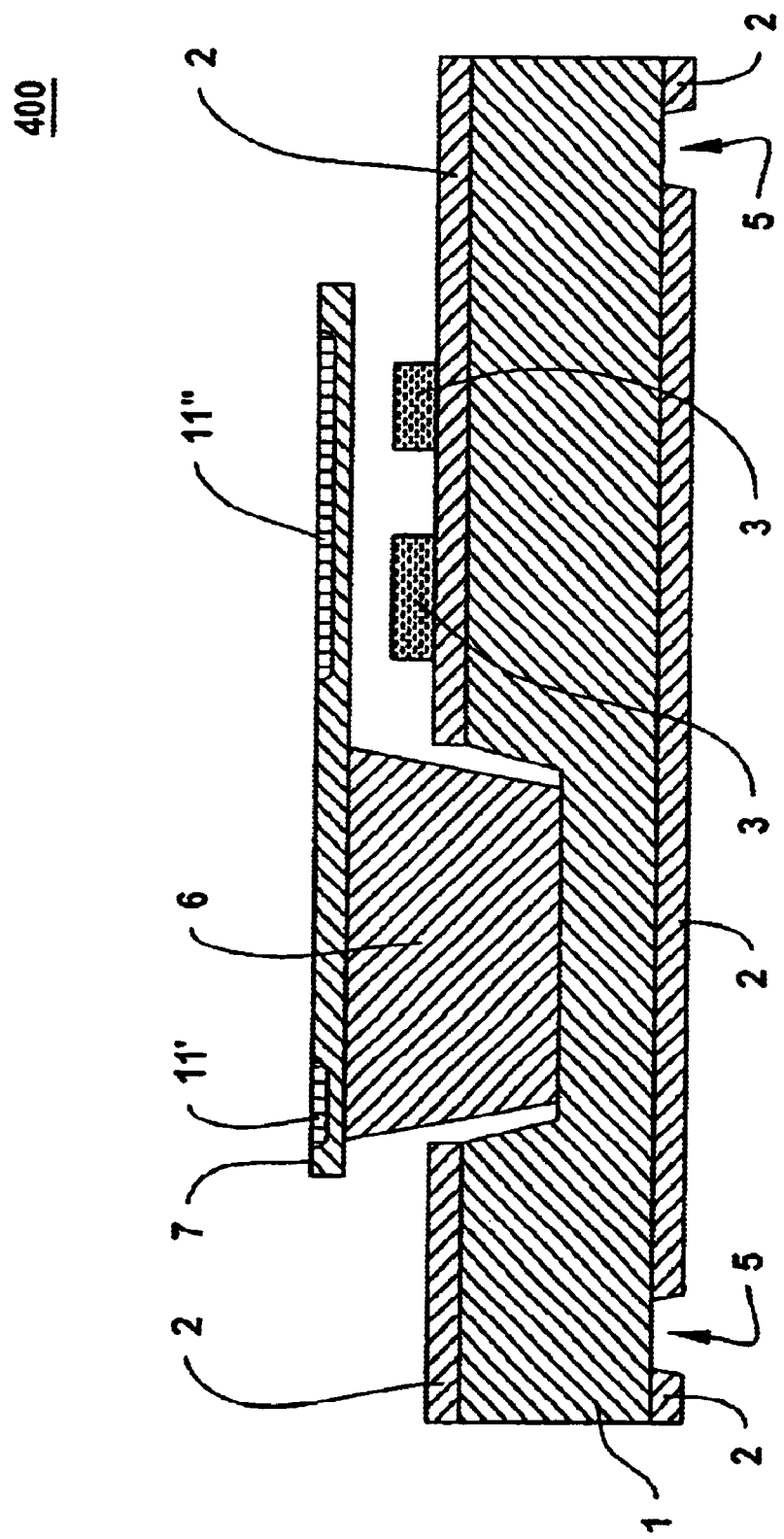
FIG. 13 is a schematic diagram illustrating the step of aligning and bonding of the starting substrate wafer and the cantilever wafer.
Figure 14:
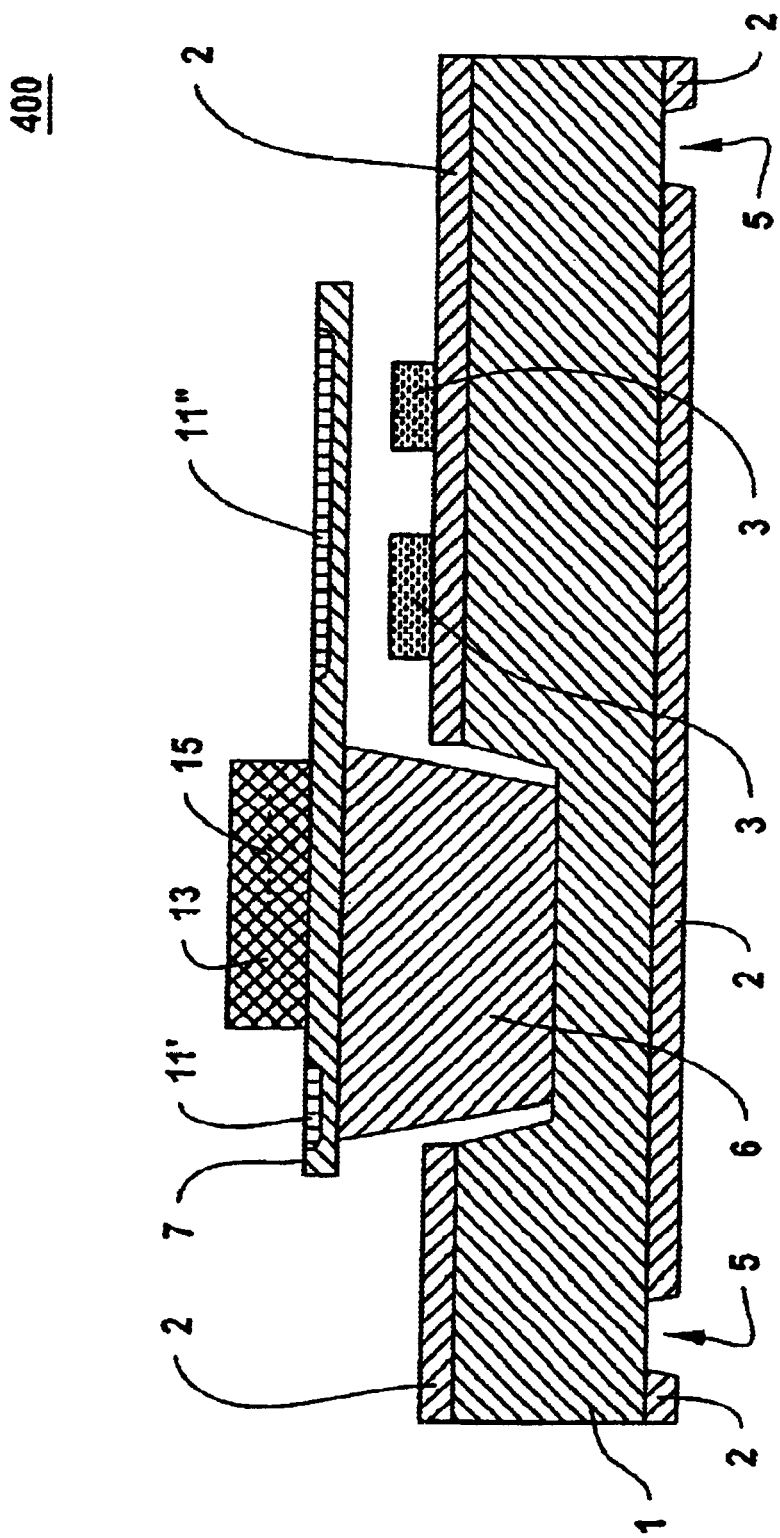
FIG. 14 is a schematic diagram illustrating the further step of assembling the sensor, comprising bonding of the microchannel plate to the assembly.

After all three starting wafers 100, 200, and 300 are fabricated as described above, the sensor 400 is finally assembled as shown on FIGS. 13 and 14.

The starting wafer 100 and the cantilever wafer 200 are aligned and bonded using a low-temperature ($\leq$600° C.) silicon-to-silicon bonding procedure so that the cantilevers 12 are located above the control and sense electrodes 3 on the starting wafer 100 (FIG. 13). The silicon-to-silicon bonding procedure is known to those skilled in the art. The alignment is achieved by using also well-known techniques.

Next, the micro-channel plate wafer 300 is aligned and bonded to the bottom assembly, also using a low temperature ($\leq$600° C.) silicon-to-silicon bond (FIG. 14).

Deep trench plasma etching is then preferably used to remove the remaining silicon substrate 13 and the oxide layer 14 of the micro-channel plate wafer 300. This completes the release of the micro-channels on the boron-doped epitaxially grown layer 7. The completed assembly is shown in FIG. 14.

Figure 15:
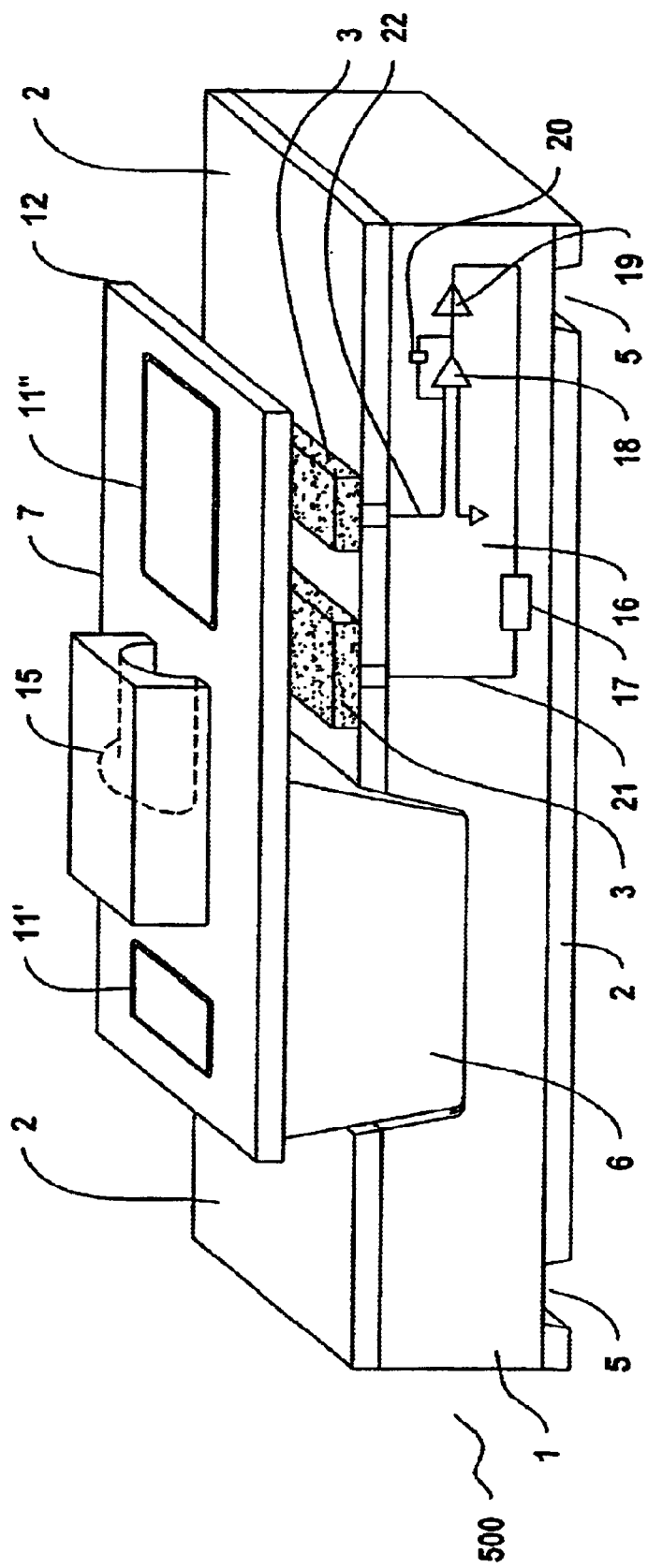
FIG. 15 is a schematic diagram showing a complete die ready for functionalization and backside etching for dicing.

The completed die ready for functionalization is shown in FIG. 15. After the die is functionalized, as described below, it is ready to perform as a sensor. The operation of the sensor can be implemented in several standard modes. For example, the control electrode can be used to electrostatically excite the cantilevers at their resonant frequencies. This oscillation frequency can be observed using the sense electrodes 3 and capacitive detection. Differential changes in the mass of the cantilevers 12 due to chemical exposure of the sensor and resulting reactions with the functionalizing layers will cause relative changes in the resonant frequencies of the cantilevers.

Since each functionalizing layer can have a different chemical selectivity, the overall selectivity of the array could be higher than that of a single cantilever functionalized with only one molecule. Alternatively, chemical changes of the functionalizing layer can cause changes in the stress of the cantilevers and this relative change in stress between different cantilevers 12 can be observed by capacitive, piezoelectric, or piezo-resistive changes. Differential detection between coated and uncoated cantilevers is advantageous in eliminating temperature sensitivity, Finally, by incorporating on-chip resistive heaters, the sensor array can be re-activated by thermally desorbing the sensed material. Thus, reuse may be possible.

An example of registering the detection, by way of a detection electrical circuit 16 known to those skilled in the art, is illustrated on FIG. 15. The circuit comprises a charge pump 17 (generating drive signal 21), amplifiers 18 and 19 and a capacitor 20. The circuit 16 detects a change in the capacitive sense signal 22 generated in the cantilever when a chemical or biological substance in the environment reacts with the already functionalized layer 11".

Figure 16:
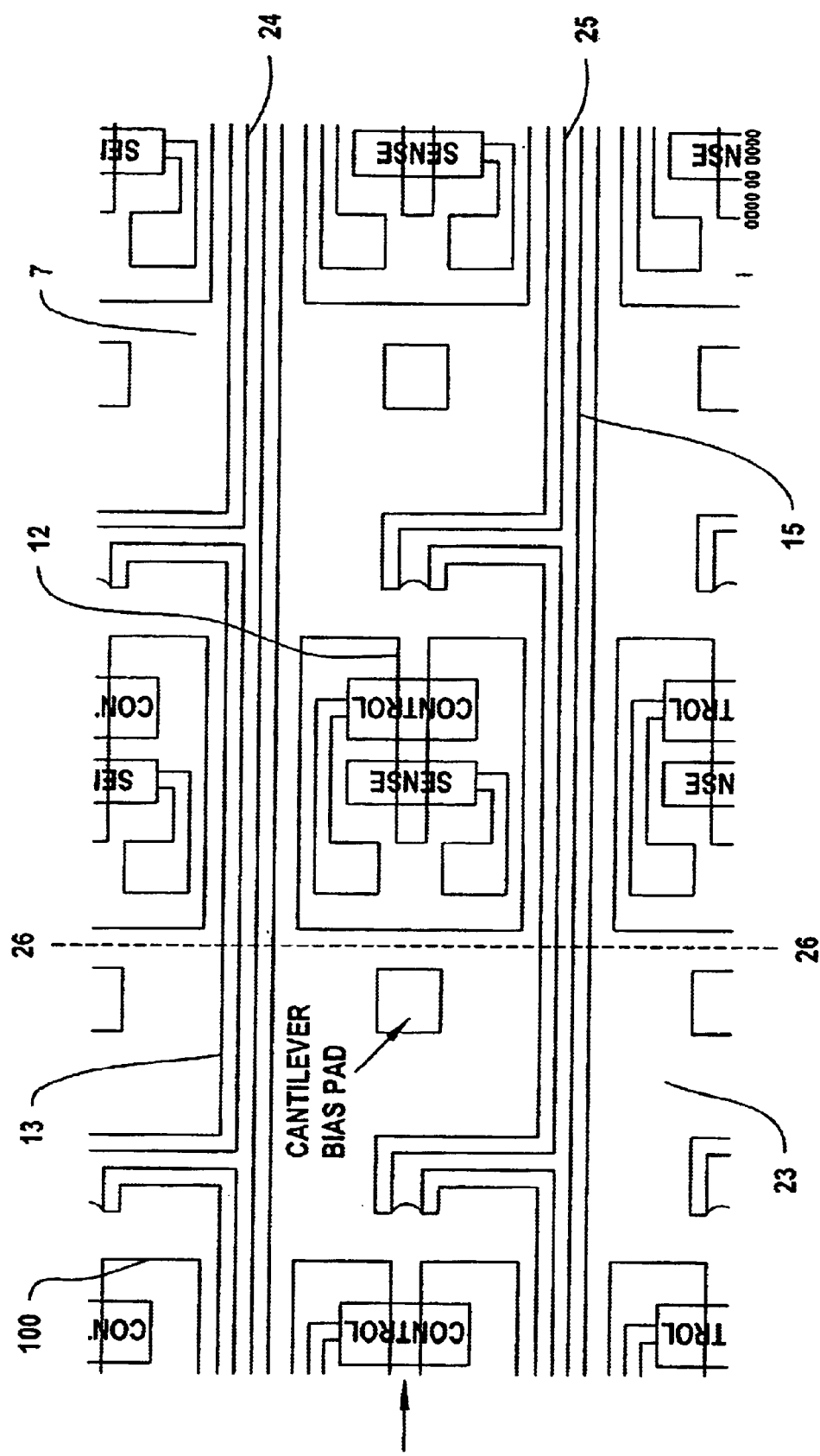
FIG. 16 is a schematic diagram showing a top view of the completed wafer.

A top view of the completed array of cantilevers is shown in FIG. 16. It shows the starting wafer 100, the micro-channels 15, the microchannel housing 13', the boron-doped layer 7 on top of the cantilever 12 and the etched regions 23 on the starting wafer 100.

A manifold (not shown) is now attached to the edge of the wafer, and a set of gases or liquid vapors that have gold-specific binding properties (e.g., sulfur or thiol group attachments) is allowed to flow through the microchannels, through the openings 24 and 25. These gases are then directed, on chip, to the appropriate cantilever, and the molecules will attach themselves to the gold seed layer located on top of each cantilever. After functionalization, the manifold is removed and the wafer is ready for final dicing.

Examples of the functionalizing materials include, but are not limited to, synthetic 5' thio-modified oligonucleotides with differing base sequences, *E. coli* serotypes, and siloxanes which will polymerize (after having adsorbed on the surface of gold), to form, for instance, polydimethylsiloxane. Those skilled in the art will know how to choose a particular set of functionalizing materials, according to their needs.

Figure 17:
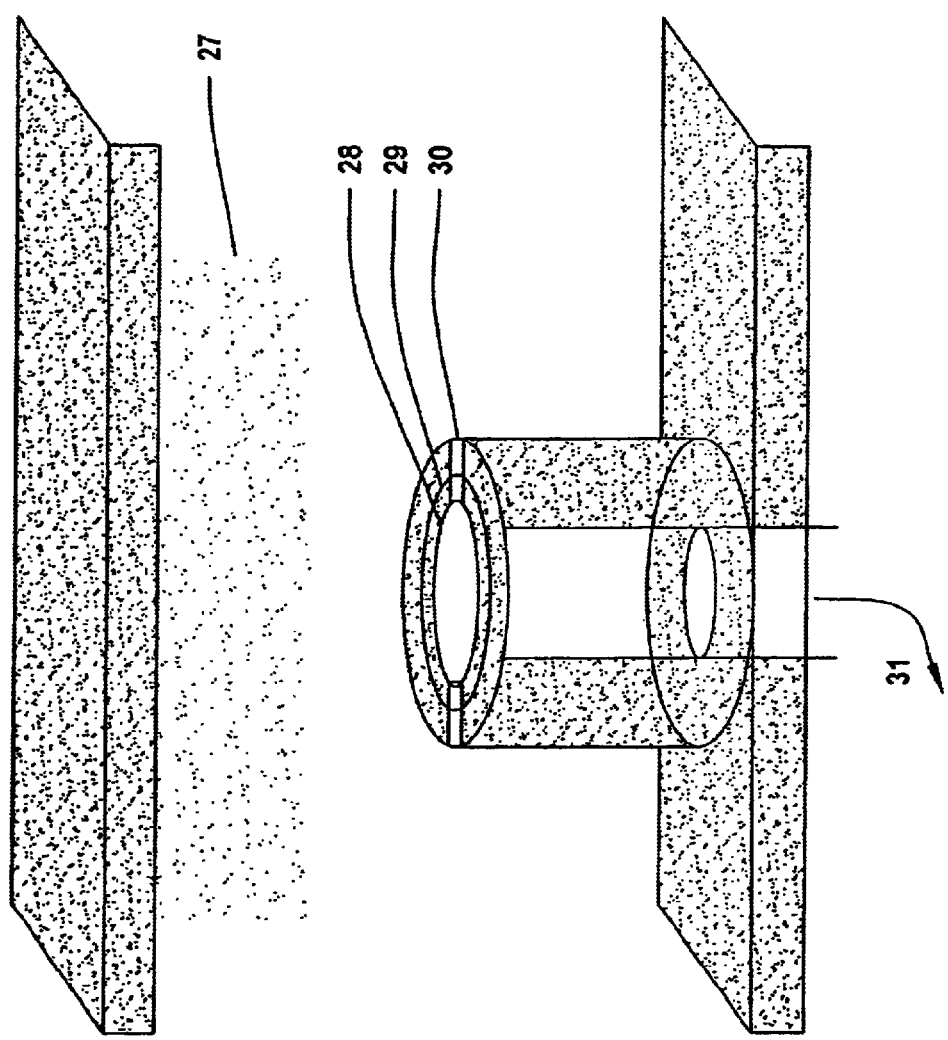
FIG. 17 is a schematic diagram showing a dicing method of this invention.

A complete die is finally diced, as shown along the line 26—26 on FIG. 16. The dicing method of this invention utilizes modifying lo a plasma etching system in which only the backside 29 of the wafer is exposed to the plasma 27, as shown on FIG. 17. This is accomplished by using an O-ring seal 28 and mounting fixture 30 in the plasma chamber so that the front side of the wafer is vacuum isolated from the etching gases. Vacuum is applied through a pump out port in direction 31. While in the plasma-etching system, the pressure is maintained to be the same on both the top and bottom sides of the wafer to prevent wafer bonding. Using the pre-etched scribe markss 5 in the bottom nitride layer 2 as a mask, the starting wafer is etched to significantly weaken the wafer along the scribe lines. After removal from the plasma etching chamber, manual cleaving of the individual dies can occur.

Having described the present invention in connection with several embodiments thereof, modification will now suggest itself to those skilled in the art. As such, the invention is not to be limited to the described embodiments except as required by the appended claims.

What is claimed is:

1. A method for fabricating a sensor, comprising steps of:
    providing a wafer comprising a plurality of cantilever assemblies, each of said assemblies comprising a cantilever member and a micro-channel plate bonded to said cantilever member, said micro-channel plate further comprising a micro-channel;
    functionalizing each of said cantilevers by directing a flow of a plurality of functionalizing materials through said micro-channels; and
    dicing said wafer into a plurality of said sensors.

2. The method as claimed in claim 1, wherein each of said cantilever assemblies further comprises:
    a substrate having a top side, a bottom side, control and sense electrodes deposited on said top side of said substrate, and scribe marks etched on said back side of said substrate, wherein
        said cantilever member has a top side, a back side, a cantilever, a seed layer, and a contact pad, said contact pad being formed on said top side of said cantilever member, said cantilever member being bonded to said substrate,
        wherein said micro-channel plate has a top side, a bottom side, and a micro-channel housing defining said micro-channel etched through said micro-channel housing, said micro-channel plate being bonded to said top side of said cantilever member.

3. The method as claimed in claim 1, wherein said functionalizing materials are directed to said cantilevers by using a manifold attached to an edge of said wafer.

4. The method as claimed in claim 2, wherein said dicing comprises the steps of:
    providing a plasma etching apparatus, said apparatus including a mounting fixture, an O-ring seal, and a vacuum chamber;
    positioning said wafer in said plasma apparatus so that said top side of said wafer is placed in vacuum; and
    using plasma to etch said wafer along said scribe marks.

5. The method as claimed in claim 2, wherein said substrate comprises a layer of a semiconducting material selected from the group consisting of silicon and Group III–Group V elements.

6. The method as claimed in claim 2, wherein said substrate has a thickness within a range of between about 650 micrometers and about 850 micrometers.

7. The method as claimed in claim 2, wherein said control and sense electrodes each comprises an adhesion layer, an active layer, and a diffusion barrier layer, said diffusion barrier layer being sandwiched between said adhesion layer and said active layer.

8. The method as claimed in claim 2, wherein said top side of said substrate is partially etched to define a trench having a bottom and, in said bonding of said cantilever member to said substrate, said cantilever member is bonded to said bottom of said trench.

9. The method as claimed in claim 2, wherein said substrate is fabricated by a process comprising the steps of:
    providing a substrate wafer having a top side and a bottom side;
    performing lithography and depositing said control and sense electrodes;
    performing lithography and etching of said top side of said substrate wafer to define a trench in said top side of said substrate wafer; and
    performing lithography and etching of said bottom side of said substrate wafer to define said scribe marks.

10. The method as claimed in claim 2, wherein said cantilever member is fabricated by a process comprising the steps of:
    providing a cantilever wafer having a front side and a back side;
    performing lithography and etching of said front side of said cantilever wafer to define open areas in said front side of said cantilever wafer and to form recesses for said seed layer and said contact pad;
    performing lithography and depositing said seed layer and said contact pad in said recesses; and
    performing lithography and etching of said back side of said cantilever wafer to release said cantilevers.

11. The method as claimed in claim 2, wherein said micro-channel plate is fabricated by a process comprising the steps of:
    providing a micro-channel wafer having a top side and a bottom side;
    performing lithography and etching of said top side of said micro-channel wafer to define said micro-channel in said top side of said micro-channel wafer; and
    performing lithography and etching of said top side of said micro-channel wafer to define said micro-channel housing.

12. The method as claimed in claim 3, wherein said functionalizing materials are selected from the group consisting of synthetic 5' thio-modified oligonucleotides with differing base sequences, E. coli serotypes, and siloxanes.

13. The method as claimed in claim 5, wherein said layer of semiconducting material is sandwiched between a layer of a masking material and a layer of an insulating material.

14. The method as claimed in claim 7, wherein said adhesion layer is fabricated of a metal selected from the group consisting of titanium and chromium, said active layer is fabricated of gold, and said diffusion barrier layer is fabricated of an other metal selected from the group consisting of platinum and palladium.

15. The method as claimed in claim 2, wherein said seed layer and said contact pad each comprises an adhesion layer, an active layer, and a diffusion barrier layer, said diffusion barrier layer being sandwiched between said adhesion layer and said active layer.

16. The method as claimed in claim 10, wherein said back side of said cantilever wafer comprises a silicon oxide, said front side of said cantilever wafer comprises a boron-doped epitaxially grown silicon layer.

17. The method as claimed in claim 10, wherein said cantilever wafer further comprises an intermediate-oxide etch stop, said front side of said cantilever wafer comprises silicon, said back side of said cantilever wafer comprises an oxide substrate.

18. The method as claimed in claim 10, wherein said cantilever wafer has a thickness within a range of between about 225 micrometers and about 325 micrometers.

19. The method as claimed in claim 13, wherein said layer of masking material and said layer of insulating material each has a thickness within a range of between about 1 micrometer and about 4 micrometers.

20. The method as claimed in claim 13, wherein said masking material is selected from the group consisting of silicon oxide and silicon nitride, and said insulating material comprises silicon nitride.

21. The method as claimed in claim 15, wherein said adhesion layer is fabricated of a metal selected from the group consisting of titanium and chromium, said active layer comprises gold, and said diffusion barrier layer is fabricated of an other metal selected from the group consisting of platinum and palladium.

22. The method as claimed in claim 2, wherein said bonding is performed at a low temperature to integrate control electronics into said starting substrate and to integrate all associated electronics with said cantilever.

23. The method as claimed in claim 22, wherein said low temperature is about 400° C.

\* \* \* \* \*